US012678159B2

(12) United States Patent
Ayub

(10) Patent No.: US 12,678,159 B2
(45) Date of Patent: Jul. 14, 2026

(54) FOUR-SPIKE STAPLER FOR SKIN WOUND CLOSURE

(71) Applicant: Hamid Ayub, Plantation, FL (US)

(72) Inventor: Hamid Ayub, Plantation, FL (US)

( * ) Notice: Subject to any disclaimer, the term of this patent is extended or adjusted under 35 U.S.C. 154(b) by 0 days.

(21) Appl. No.: 19/198,376

(22) Filed: May 5, 2025

(65) Prior Publication Data

US 2026/0130667 A1 May 14, 2026

Related U.S. Application Data

(63) Continuation-in-part of application No. 18/945,770, filed on Nov. 13, 2024, now Pat. No. 12,383,261.

(51) Int. Cl.
A61B 17/064 (2006.01)
A61B 17/072 (2006.01)

(52) U.S. Cl.
CPC .... A61B 17/0644 (2013.01); A61B 17/07207 (2013.01); *A61B 2017/0641* (2013.01); *A61B 2017/07242* (2013.01)

(58) Field of Classification Search
CPC ... A61B 17/068; A61B 17/064; B25C 5/1603; B25C 5/025
See application file for complete search history.

(56) References Cited

U.S. PATENT DOCUMENTS

| | | | | | |
|---|---|---|---|---|---|
| 4,467,805 | A | * | 8/1984 | Fukuda | A61B 17/0684 606/217 |
| 4,610,251 | A | * | 9/1986 | Kumar | A61B 17/0644 411/460 |
| 6,726,695 | B2 | * | 4/2004 | Tong | A61B 17/068 606/151 |
| 11,253,252 | B2 | * | 2/2022 | Kubiak | A61B 17/0466 |

* cited by examiner

*Primary Examiner* — Nathaniel C Chukwurah

(57) ABSTRACT

The present invention discloses a medical stapler designed for efficient wound closure, utilizing a four-legged staple assembly. The staple assembly comprises four symmetrically positioned legs—two longer or standard legs for engaging deeper tissue layers and two shorter legs for securing superficial skin layers—each configured to penetrate tissue at an angle of approximately 90 degrees±15 degrees relative to the tissue surface. The staple is formed as a continuous, one-piece biocompatible metallic structure with a central apex that uniformly distributes compression forces across the wound site. This design enables simultaneous closure of multiple tissue depths in a single deployment, enhancing surgical efficiency. The symmetrical leg spacing ensures even tissue engagement, while the configuration resists rotational movement within tissue, improving post-deployment stability. Additionally, the design minimizes the risk of skin overlap, puckering, and tissue misalignment, supporting a more aesthetically pleasing wound closure.

8 Claims, 3 Drawing Sheets

Medical
Stapler (100)

Enclosed body with
staple assembly (102)

After insertion →

FOUR-SPIKE STAPLER FOR SKIN WOUND CLOSURE

CROSS-REFERENCE TO RELATED APPLICATION

This application is a Continuation-in-Part (CIP) of U.S. patent application Ser. No. 18/945,770, filed on Nov. 11, 2024, now U.S. Pat. No. 12,383,261 B1, which is a Continuation-in-Part (CIP) of U.S. Pat. No. 12,089,840 B2, filed on 11 Feb. 2024 and issued Sep. 17, 2024, the disclosure of which is hereby incorporated by reference in its entirety in this application.

FIELD OF INVENTION

Embodiments of a present disclosure relate to the field of surgical instruments and more particularly to a surgical stapler for approximation of skin and deeper tissues.

BACKGROUND

Conventional surgical skin staples typically have two spikes or legs and are generally U-shaped. After being deployed, such staples form a rectangular shape, which may turn within the skin, or may buckle. This deployment can lead to overlapping or misalignment of the wound edges, potentially causing unpleasant cosmetic outcomes.

US20020133181A1 discloses a four-spike staple comprising two longer outer spikes and two shorter inner spikes. The shorter inner spikes serve to stabilize the skin and help prevent overlapping of the wound edges. However, systems incorporating such staples may also require additional stabilizing components that extend beneath the skin surface. Upon removal, these components may necessitate manual suturing or be left open, which can result in patient discomfort, potentially increased healing time, or aesthetically unfavourable scarring.

To address the concerns in the background, an effective way for wound closures is required.

SUMMARY

This summary is provided to introduce a selection of concepts, in a simple manner, which is further described in the detailed description of the disclosure. This summary is neither intended to identify key or essential inventive concepts of the subject matter nor to determine the scope of the disclosure.

The present invention discloses a medical stapler configured to deploy a single, integrally formed surgical staple comprising four legs—two longer legs intended to anchor into the underlying tissue and two shorter legs designed to engage with the superficial skin layers. Unlike conventional four-legged staples disclosed in the prior art, such as those forming an "M" shape with legs angled at approximately 60 degrees—may require excessive pressure for full engagement—the staple of the present invention features legs oriented to penetrate the tissue or skin at approximately 90 degrees (with an allowable deviation of ±15 degrees). This near-perpendicular configuration improves deployment stability, minimizes tissue buckling, and enhances alignment of skin edges, resulting in better cosmetic outcomes. The differential leg lengths facilitate a dual-level closure, offering deep tissue anchoring alongside precise approximation of the skin layers. Moreover, unlike prior art systems which rely on stabilizers extending beneath the skin—potentially requiring manual suturing upon removal or leaving open areas that may scar. The present invention achieves stabilization and closure without introducing such additional invasive components.

The surgical staple is formed from a continuous metallic structure configured into a 'Square Arch' design. This single-piece architecture enhances deployment precision and reliability, while also simplifying both the manufacturing and operational aspects of the stapler. The preferred materials for the staple include surgical-grade stainless steel, titanium alloy, biocompatible metals or absorbable material that are selected for their mechanical strength, corrosion resistance, and that are compatibility with human tissue.

The medical stapler is configured to apply this staple in a controlled and uniform manner. Its internal mechanism enables secure, perpendicular deployment of the legs into the tissue, reducing the risk of misalignment and minimizing trauma. The central apex of the staple serves to evenly distribute compressive forces across the wound, further supporting wound healing and tension balance along the incision line.

This design is particularly effective in maintaining consistent pressure and alignment between opposing skin edges, resulting in neater closures and reducing the likelihood of skin inversion or puckering. By enabling even tension distribution and improved approximation, the stapler-staple system supports better wound healing outcomes and offers a more cosmetically favourable alternative to traditional suturing methods.

An object of the present invention is to provide a surgical staple that can help minimizes skin distortion and supports improved post-operative healing. Another object is to introduce a structurally simplified, single-piece staple that ensures consistent, reliable deployment. The combined design of the stapler and its corresponding staple offers a robust, efficient, and user-friendly solution for surgical wound closure.

A further object of the present invention is to expedite the wound closure process during surgical procedures, thereby significantly reducing the time required to complete skin and tissue approximation. This, in turn, minimizes the overall duration for which the patient is maintained under anaesthesia, contributing to improved surgical efficiency and reduced anaesthesia-related risks.

Unlike prior art that utilizes spikes at a 60 degrees angle for insertions, the present design distributes pressure evenly across the wound and maintains proper skin alignment with potential minimal risk of overlapping or edge inversion. The one-piece construction also improves structural integrity and reduces component failure.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF DRAWINGS

The disclosure will be described and explained with additional specificity and detail with the accompanying figures in which.

Figure 1:
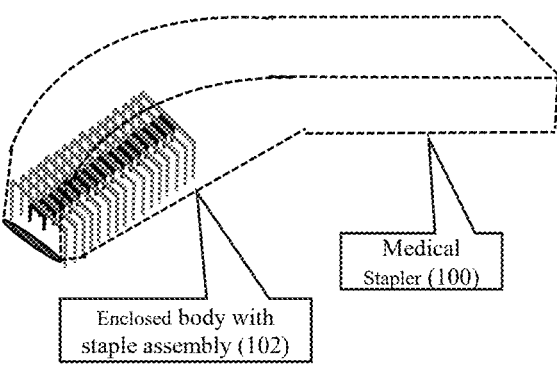
FIG. 1 is a schematic diagram illustrating a medical stapler (100) designed in accordance with an embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION OF THE DISCLOSURE

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure. It will be understood by those skilled in the art that the foregoing general description and the following detailed description are exemplary and explanatory of the disclosure and are not intended to be restrictive thereof.

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

The terms "comprise", "comprising", or any other variations thereof, are intended to cover a non-exclusive inclusion, such that one or more devices or sub-systems or elements or structures or components preceded by "comprises . . . a" does not, without more constraints, preclude the existence of other devices, sub-systems, additional sub-modules. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

The present disclosure provides a medical stapler for wound closure comprising a four-legged staple assembly, wherein each staple includes two longer or standard legs and two shorter legs. The longer legs are configured to penetrate and secure deeper tissue layers, while the shorter legs are adapted for engaging superficial skin layers. The four legs are symmetrically positioned and spaced equidistantly around a central apex. Each leg is designed to enter tissue at an angle of approximately 90 degrees±15 degrees relative to the tissue surface. The central apex is formed in a Square Arch configuration, which serves to uniformly distribute compression forces across the wound site, promoting optimal tissue approximation and healing. The staple assembly is formed as a continuous, one-piece biocompatible metallic structure without joints or seams. The staple is configured to resist rotation within the tissue post-deployment, ensuring stable approximation and minimizing misalignment. The uniform spacing of the legs ensures even penetration and consistent closure across the wound site. Additionally, the configuration enables secure multi-depth closure in a single deployment, thereby expediting the wound closure process. As a result, overall surgical time is reduced, minimizing the duration of anaesthesia exposure and improving procedural efficiency and patient safety.

FIG. 1 is a schematic diagram illustrating a medical stapler (100) designed in accordance with an embodiment of the present disclosure. The medical stapler (100) is configured to deploy a four-legged staple assembly (102) to close wounds or tissue layers. The staple assembly comprises a continuous, one-piece metallic structure formed into a "Square Arch"-shaped configuration. This shape enables more controlled and perpendicular penetration compared to angled or M-shaped designs in prior art, which often require additional force to straighten and may result in uneven closure.

As shown in the figure, the staple assembly (102) includes two inner legs and two outer legs symmetrically positioned beneath the central apex. The inner legs are slightly angled or curved inward relative to the outer legs, allowing for differentiated depth engagement and improved stabilization of the wound site. The uniform spacing and symmetrical positioning of all four legs ensure balanced tissue compression and minimize the risk of skin overlap, puckering, or misalignment. The central apex, being continuous and free of joints or seams, distributes compression forces evenly across the wound, resulting in consistent closure and enhanced healing outcomes. This staple configuration allows for effective closure of multiple tissue layers with a single deployment action, enhancing both surgical efficiency and cosmetic results.

The staple is preferably made from surgical-grade stainless steel, titanium alloy, or other biocompatible materials recognized for their strength, corrosion resistance, and tissue compatibility. The four legs of the staple are integrally formed as part of a single unit, with two longer (standard) legs designed to anchor deeper into tissue and two shorter (fine) legs intended for superficial engagement with the skin. This variation in leg length enhances wound edge alignment while minimizing tissue buckling. The stapler (100) includes a mechanism for securely deploying the staple in a manner that ensures perpendicular insertion of each leg, thereby promoting precise closure and improved cosmetic outcomes.

Figure 2:
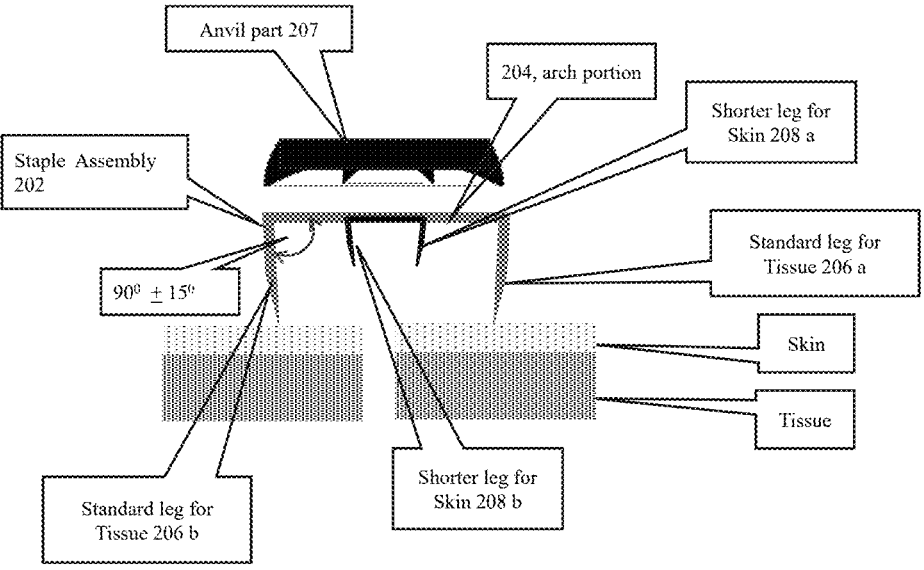
FIGS. 2A and 2B provides a detailed view of the four-legged staple (202) deployed by the medical stapler in accordance with an embodiment of the present disclosure.
Figure 2:
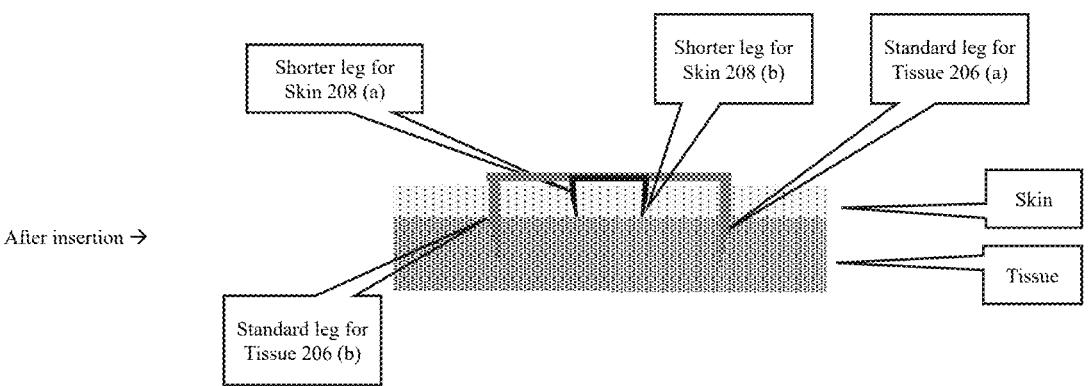

FIGS. 2A and 2B provides a detailed view of the four-legged staple assembly (202) deployed by the medical stapler (100) of FIG. 1. FIG. 2A illustrates the medical stapler, which is configured to deploy a specialized four-legged staple assembly (202) designed for approximating tissue layers and facilitating effective wound closure. The medical stapler (100) and staple assembly (202) are designed to improve wound edge alignment, minimize tissue trauma, and enhance cosmetic and healing outcomes.

The staple assembly (202) comprises a unitary metallic structure formed into a generally square or rectangular arch configuration. The upper horizontal segment of the staple (204), also referred to as the crown or arch portion, connects four downward-projecting legs. Unlike conventional M-shaped or bent wire staples that often require post-deployment deformation or suffer from uneven force distribution, the square-arch shape of staple (202) allows for precise, symmetric deployment with improved mechanical integrity.

The staple 202 includes four integrally formed legs extending downward from an arch portion 204. Upon actuation of the stapling device, the staple 202 is driven against an anvil 207. The anvil 207 is configured to facilitate precise and symmetric deformation of the staple 202, thereby improving mechanical integrity of the formed staple structure and promoting uniform tissue approximation. The outermost pair, identified as longer or standard-length legs (206a, 206b), are positioned at the lateral ends of the staple and are configured to penetrate deeper into subcutaneous tissue. The inner pair, referred to as shorter or fine-length legs (208a, 208b), are located more centrally beneath the arch and are designed to engage only the dermal or superficial skin layers. Each of the four legs is oriented to enter tissue perpendicularly or at an angle within the range of approximately 90°±15° relative to the surface of the tissue. This angular tolerance ensures that the staple (202) achieves near-vertical insertion, promoting stable and uniform tissue engagement across both superficial and deeper layers. The perpendicularity of the leg orientation reduces stress concentration, minimizes tissue buckling, and facilitates optimal healing. The staple (202) is preferably fabricated from biocompatible metallic materials such as surgical-grade stainless steel, titanium, or titanium alloys. These materials offer the necessary strength, corrosion resistance, and biological compatibility required for wound closure applications, while minimizing risks of rejection or inflammation.

The medical stapler (100) houses a deployment mechanism designed to retain, guide, and eject the staple (202) with precision. This mechanism ensures that all four legs—longer legs (206a, 206b) and shorter legs (208a, 208b) are driven into the tissue simultaneously and within the defined angular range. The controlled deployment reduces application force, enhances staple alignment, and promotes consistent wound closure. The described staple configuration enables dual-plane wound engagement: the longer legs (206a, 206b) provide deep tissue anchoring, while the shorter legs (208a, 208b) maintain surface approximation. This asymmetry, combined with the 90°±15° insertion angle and square-arch geometry, ensures that tension is distributed evenly across the wound site, resulting in a more secure closure and aesthetically favorable healing.

FIG. 2B illustrates the configuration of the four-legged staple following its deployment into tissue at the wound site. The described staple configuration enables dual-plane wound engagement, wherein the longer or standard legs (206a, 206b) provide deep tissue anchoring through penetration into subcutaneous layers, while the shorter legs (208a, 208b) engage the more superficial dermal or epidermal layers to maintain surface approximation. Upon deployment from the medical stapler, the staple transitions into a fully inserted state in which all four legs penetrate and engage distinct tissue depths to achieve stable wound closure. This staggered leg length supports simultaneous approximation of multiple tissue planes, enhancing overall holding strength and reducing the risk of wound edge separation during healing. Each leg is oriented to penetrate the tissue at an angle of approximately 90 degrees±15 degrees relative to the skin surface, enabling precise, perpendicular entry that minimizes disruption to surrounding tissue and maintains proper wound edge alignment. This configuration reduces the potential for adverse cosmetic outcomes such as skin inversion, eversion, or puckering. The central square-arch portion of the staple, which remains slightly raised above or flush with the epidermis, is configured to distribute compressive forces uniformly across the wound site. This even distribution of pressure contributes to haemostasis, minimizes tissue trauma, and reduces the likelihood of wound dehiscence.

The symmetrical design and uniform spacing of the four legs ensure balanced tension distribution, preventing localized stress and supporting consistent tissue approximation. Once deployed, the staple is retained securely within the tissue and demonstrates enhanced resistance to rotational or lateral displacement—particularly advantageous in anatomical regions subject to high mobility or tension. The sharp, pointed tips of each leg facilitate controlled and low-resistance penetration, further minimizing trauma during insertion. In certain embodiments, the staple may also accommodate minor conformational adjustments post-deployment, allowing for compliance with tissue curvature or compression without compromising its structural integrity.

According to an exemplary embodiment, the device comprises a medical stapler specifically designed for use in surgical procedures. The four-legged staple assembly is configured to close skin, tissue, or internal organs with minimal trauma, offering a reliable and efficient alternative to traditional sutures. The four-legged staple may be formed from biocompatible materials such as stainless steel or titanium, ensuring safety and compatibility with human tissue. In this embodiment, the medical stapler is used to apply the four-legged staple in a controlled manner, ensuring consistent placement and secure closure. This reduces the risk of infection, minimizes tissue damage, and promotes faster healing, making it an ideal solution for various surgical applications.

In an embodiment, the medical stapler includes a staple assembly comprising a central apex formed in a "Square Arch" configuration. This design is configured to distribute compression forces uniformly across the wound site while facilitating substantially perpendicular penetration of the staple legs into the tissue. In contrast to the "M" or "W" shaped configurations known in the prior art—which may necessitate excessive deployment force to achieve straightening and often require a stabilizing component that, upon removal, can create residual openings in the skin requiring additional closure measures or potentially resulting in undesirable scarring. The Square Arch structure provides a more controlled and consistent tissue engagement. This reduces localized trauma and enhances the reliability and effectiveness of wound closure.

In further embodiments, other variations of the central apex shape may be utilized, provided they maintain the functional objective of uniform force distribution and enhanced deployment efficiency. It is understood that in other embodiments, variations in the leg dimensions may be employed, such as legs with different lengths or thicknesses, to accommodate specific wound types or surgical requirements, while still achieving a stable and effective wound closure.

In a further embodiment, the staple assembly is configured to resist rotation within the tissue after deployment. This configuration ensures stable tissue approximation and minimizes the potential for misalignment. Other embodiments may include additional features such as friction elements, interlocking mechanisms, or alternative methods to achieve resistance to rotation, depending on the specific requirements of the surgical procedure.

Additionally, in an embodiment, the spacing between adjacent legs of the staple assembly is uniform, allowing for even penetration of the tissue and consistent closure across the wound site. It is contemplated that variations in the spacing between the legs may be employed in other embodiments, depending on the size and nature of the wound, while still ensuring consistent and effective tissue closure.

In one embodiment, a surgical staple for wound closure comprises an arch portion configured to span across a wound site. Extending downward from opposite lateral ends of the arch portion is a first pair of legs, each having a first length suitable for penetrating into subcutaneous tissue. A second pair of legs extends downward from a central region of the arch portion between the first pair of legs, each leg of the second pair having a second length that is shorter than the first length and is configured to engage only the dermal layer of tissue. The four legs are oriented to enter tissue in a substantially perpendicular direction, or within an angular range of approximately 90°±15° relative to the tissue surface. With pressure applied from an anvil, the staple is deployed in a symmetric fashion, enabling uniform engagement across superficial and deeper layers, improving mechanical integrity, and reducing stress concentrations at the wound site.

The advantages of the described medical stapler invention include:

Symmetrical and Uniform Skin Closure: The medical stapler utilizes a four-legged staple assembly with two fine-length inner legs and two standard-length outer legs, all oriented symmetrically. This configuration ensures uniform penetration of the skin and subcutaneous tissue and allows for consistent approximation of the wound edges, minimizing the risk of overlap or misalignment.

Improved Cosmetic Results: Each leg of the staple assembly is configured to penetrate the skin at an angle of approximately 90°±15° relative to the tissue surface. This angular configuration reduces the risk of skin inversion, eversion, or puckering during closure, and promotes a more precise tissue approximation. The result will potentially be smoother and more aesthetically pleasing wound closure.

Even Distribution of Compression Forces: The square-arch geometry of the staple, in conjunction with the uniform leg spacing and length differentiation, enables the central apex of the staple to distribute compression forces evenly across the wound site. This balanced pressure enhances tissue approximation, reduces the risk of wound dehiscence, and promotes efficient healing.

Enhanced Rotational Stability: The four-legged configuration of the staple assembly provides increased contact with tissue across multiple planes, minimizing the risk of rotational displacement post-deployment. This stability ensures that the wound edges remain aligned during the healing process, supporting optimal functional and cosmetic outcomes.

Simplified Manufacturing: The staple assembly is formed from a single, continuous metallic structure without joints or seams. The use of a square-arch profile further simplifies bending operations during manufacturing and enhances structural integrity, reducing failure points when compared to multi-component or M-shaped staples.

Reliable Penetration and Pressure Distribution: The uniform thickness and biocompatible material composition of all four legs—regardless of length—ensure consistent penetration into the targeted tissue layers. The dual-leg length design allows for simultaneous engagement of both skin and deeper tissue while maintaining even pressure distribution across the closure site, thereby minimizing tissue trauma.

Ease of Use: The medical stapler (100) is designed to be compatible with existing surgical stapling systems, facilitating straightforward adoption in operating room environments. The deployment mechanism ensures simultaneous and accurate delivery of all four legs within the designated 90°±15° angle, requiring no special training or tools for implementation.

Versatility for Various Surgical Applications: The four-legged staple assembly is particularly suited for surgeries where both multi-layer closure and cosmetic outcome are essential or desirable. Its ability to secure skin and subcutaneous tissue layers concurrently increases its utility across general and specialized surgical fields.

Durable and Biocompatible Material: The staple assembly is preferably constructed from surgical-grade stainless steel, titanium, or titanium alloys. These materials are corrosion-resistant, biocompatible, and capable of withstanding physiological loads without deformation, thereby reducing the risk of infection, inflammation, or delayed healing.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar terms are intended to be equivalent in meaning and be open-ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present disclosure are intended to be illustrative, but not limiting, of the scope of the invention, which is set forth in the following claims.

What is claimed is:
1. A medical stapler for wound closure, comprising:
a four-legged staple assembly, wherein each staple comprises:
two longer legs and two shorter legs, the longer legs being configured to penetrate and hold deeper tissue layers, and the shorter legs being adapted for superficial skin engagement;

wherein the four legs are symmetrically positioned and spaced equidistantly around a central apex;

wherein each leg is configured to penetrate the tissue at an angle of approximately 90 degrees #15 degrees relative to the tissue surface.

2. The medical stapler of claim 1, wherein the central apex is formed in a Square Arch configuration a shape being configured to uniformly distribute compression forces across the wound site, thereby promoting optimal tissue approximation and healing.

3. The medical stapler of claim 1, the central apex forms a continuous, one-piece biocompatible metallic structure with no joints or seams, the central apex being shaped in a square arch configuration.

4. The medical stapler of claim 1, wherein the four legs of the staple assembly include two longer legs adapted for engaging deeper tissue layers and two shorter legs adapted for engaging superficial skin layers, thereby enabling secure multi-depth closure and improved skin edge approximation.

5. The medical stapler of claim 1, wherein the staple assembly is adapted to achieve simultaneous closure of both superficial and subdermal tissue layers in a single deployment.

6. The medical stapler of claim 1, wherein the staple assembly is configured to resist rotation within the skin after deployment, maintaining stable tissue approximation and minimizing misalignment.

7. The medical stapler of claim 1, wherein the spacing between adjacent legs of the staple assembly is uniform, ensuring even penetration of the tissue and consistent closure across the wound site.

8. A surgical staple for wound closure, comprising:

an arch portion configured to span across a wound site;

a first pair of legs extending downward from opposite lateral ends of the arch portion, each leg of the first pair having a first length;

a second pair of legs extending downward from a central region of the arch portion between the first pair of legs, each leg of the second pair having a second length shorter than the first length;

wherein the four legs are configured to be driven into tissue using an anvil to facilitate symmetric deployment; and wherein each of the four legs is oriented at an angle within +15° of perpendicular relative to the surface of the tissue.

* * * * *